US006331298B1

(12) United States Patent
Ferguson et al.

(10) Patent No.: US 6,331,298 B1
(45) Date of Patent: Dec. 18, 2001

(54) WOUND HEALING AND TREATMENT OF FIBROTIC DISORDERS

(75) Inventors: Mark William James Ferguson, Stockport; Mamta Shah, Withington, both of (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 08/307,640

(22) PCT Filed: Mar. 22, 1993

(86) PCT No.: PCT/GB93/00586

§ 371 Date: Sep. 16, 1994

§ 102(e) Date: Sep. 16, 1994

(87) PCT Pub. No.: WO93/19769

PCT Pub. Date: Oct. 14, 1993

(30) Foreign Application Priority Data

Mar. 28, 1992 (GB) .................................................. 9206861

(51) Int. Cl.⁷ .................................................... A61K 45/00
(52) U.S. Cl. .................. 424/85.1; 424/145.1; 424/158.1
(58) Field of Search .............................. 424/130.1, 145.1, 424/85.1, 158.1; 530/387.1, 388.23, 388.24, 350, 351; 514/12

(56) References Cited

U.S. PATENT DOCUMENTS 5,155,214 * 10/1992 Baird ..................................... 530/399

FOREIGN PATENT DOCUMENTS

| 0375127 | 11/1989 | (EP) . |
| 0433225 | 11/1990 | (EP) . |
| 9003810 | 4/1990 | (WO) . |
| 9110727 | 7/1991 | (WO) . |
| 9217206 | 10/1992 | (WO) . |

OTHER PUBLICATIONS

Stull et al. Pharmaceutical Research, vol. 12:465–483, 1995.*

Waldmann, Annual Review of Immunology, vol. 10:675–704, 1992.*

Abstract for WO 90/10448–A; Sep. 20, 1990 (9040).

Abstract for WO 91/04319–A; Apr. 4, 1991 (9116).

Abstract for WO 91/18624–A; Dec. 12, 1991 (9201).

* cited by examiner

Primary Examiner—Patrick J. Nolan
(74) Attorney, Agent, or Firm—Nixon & Vanderhye P.C.

(57) ABSTRACT

A healing composition containing at least one non-fibrotic growth factor in combination with a pharmaceutically acceptable carrier is disclosed. A method of preparation of the composition and method of treating a host, suffering from a wound or fibrotic condition, disease, disorder with the composition is also disclosed.

12 Claims, No Drawings

WOUND HEALING AND TREATMENT OF FIBROTIC DISORDERS

This application is a 35 USC 371 National Stage Application of PCT/GB93/00586.

This invention concerns the healing of wounds and other conditions in which fibrosis is a major mechanism of tissue repair or where excessive fibrosis leads to pathological derangement and malfunctioning of the tissues. It refers in particular to agents and techniques for facilitating repair and healing of animal tissues, without excessive fibrosis, and for preventing or treating diseases and conditions of fibrosis.

Fibrosis is a major problem in wound healing causing scarring of the tissue, which not only looks unsightly, but also causes problems in respect of growth of the tissue, function, movement etc. This is particularly true following injuries to children or following major burns.

In addition, fibrosis is a major medical problem where abnormal or excessive deposition of fibrous tissue occurs in many diseases, including liver cirrhosis, glomerulonephritis, pulmonary fibrosis, systemic fibrosis, rheumatoid arthritis, as well as wound healing.

The mechanism of fibrosis is still not fully understood, but wound healing usually begins as an inflammatory reaction with leucocyte infiltration and accumulation of cytokines. These cytokines are responsible for the proliferation of fibroblasts and the deposition of extracellular matrix proteins (including collagen and fibronectin) which accumulate and result in permanent alteration in tissue structure and function.

Examples of the regulatory cytokines include tumor necrosis factor (TNF), fibroblast growth factors (FGF's), platelet derived growth factor (PDGF) and transforming growth factor β (TGFβ), (TGFβ-1 to TGFβ-5 have so far been identified). Two of these cytokine families TGFβ and PDGF, have been reported to be highly fibrogenic, and, moreover, inhibition of two of the TGFβ's and PDGF activity, using anti-TGFβ-1, anti-TGFβ-2 and anti-PDGF antibodies, has been shown to diminish fibrosis in tissue injury (Shah el al, The Lancet, 339, 213–214, 1992; WO 91/04748).

The present invention provides novel compositions useful in the treatment of wounds and fibrotic disorders and which may prevent, inhibit or reverse fibrosis.

The invention comprises a healing composition containing at least one non-fibrotic growth factor in combination with a pharmaceutically acceptable carrier.

The composition may comprise TGFβ-3 as the or a non-fibrotic growth factor, such that on application of the composition to the tissue, this non-fibrotic growth factor is present in an elevated level compared to its naturally occuring level.

The composition may comprise acidic or basic FGF as the or a non-fibrotic growth factor, again resulting in a much elevated level of non-fibrotic growth factor than would naturally be present.

The composition may comprise anti-fibrotic agents, such as fibrotic growth factor neutralising agents, for example antibodies to TGFβ-1, TGFβ-2 and PDGF; binding proteins which prevent TGFβ-1, TGFβ-2 and PDGF from binding to their receptors by either binding to the growth factor itself, eg. Decorin, Biglycan, or binding to the receptor, eg. peptides containing the receptor binding site sequence or soluble forms of the growth factor receptors and the growth factor binding domains of these receptors; and antisense oligo-nucleotides or ribosymes which act to prevent fibrotic growth factor mRNA translation.

The composition may comprise combinations of non-fibrotic growth factors, for example, TGFβ-3 and anti-fibrotic agents, for example, anti-TGFβ-1 and anti-TGFβ-2.

The non-fibrotic growth factor and/or anti-fibrotic agent(s) may be present in the composition in an active or inactive form. Inactivation may be by any of a number of mechanisms, for example, by encapsulation. Capsules may be degradeable by an external stimulus to release the active form when required. The external stimulus may include UV light, ultrasound, in vivo enzymes or heat.

Inactivation may, however, be by the molecular addition of a binding molecule. The binding molecule may be detachable when required by an external stimulus such as UV light, ultrasound, in vivo enzymes or heat.

The non-fibrotic growth factor may be present in an inactive form, for example, as a precursor, and may be activated upon contact with tissue containing the natural cleavage enzymes required to convert the precursor into its active form.

The carrier may comprise a neutral sterile cream, gel, aerosol or powder for topical application, or may be in the form of a patch, sterile dressing or an absorbable dressing. The carrier may be a biopolymer of collagen, hyaluronic acid or polymer of PVC to which the anti-fibrotic or non fibrotic agents are attached in such a way as to facilitate their action and/or release when the carrier is in contact with or implanted into either the wound or fibrotic lesion. The carrier may also comprise a sterile solution for irrigation, injection either locally or systemically or inhalation, or may be in the form of a tablet, capsule, and the like, for enteral administration.

The present invention also provides a method of preparation of a pharmaceutical healing or anti-fibrotic composition containing at least one non-fibrotic growth factor for topical application in a cream, gel, aerosol, powder, patch, dressing, biopolymer or polymer implant, delay or slow release system, or in a solution for irrigation, injection or inhalation, or in a tablet or capsule for enteral administration.

The present invention also provides a method of inhibiting fibrosis during the healing of wounds and in other fibrotic conditions and disorders, for example ulcers, comprising administering to a host suffering from tissue wounding or other fibrotic conditions and disorders, at least one non-fibrotic growth factor.

The present invention also provides a method of reversing fibrosis in such fibrotic conditions and disorders comprising administering to a host suffering from such fibrotic conditions and disorders, at least one non-fibrotic growth factor, for example, TGFβ-3 and/or at least one anti-fibrotic agent for example, anti-TGFβ-1/TGFβ-2.

As mentioned above, two cytokines have been identified as being involved in fibrosis, namely PDGF and TGFβ. Of these two, TGFβ appears to play the major role. For example, in tissues which heal without scar formation, such as fetal and embryonic wounds where there is a lowered inflammatory response and altered cytokine profile, the level of TGFβ in particular, is much reduced.

TGFβ comprises a family of molecules, the important mammalian members being TGFβ-1, TGFβ-2 and TGFβ-3 (Roberts and Sporn, The Transforming Growth Factor-βs, In: Peptide Growth Factors and their Receptors, Springer Verlag, Berlin, 1990, p418–472). The TGFβs, although having different patterns of expression, share over 70% peptide homology and are thought to have similar functions and act inter-changeably. Thus in wound healing it would be expected that TGFβ-3 would act like TGFβ-1 and TGFβ-2 to increase extracellular matrix production, angiogenesis and the inflammatory response.

As discussed above, fibrotic disease is a major medical problem. In such diseases, there is abnormal or excessive deposition of fibrous tissue. Such diseases are exemplified by liver cirrhosis, glomerulonephritis, pulmonary fibrosis, systemic fibrosis and rheumatoid arthritis. In such diseases the use of TGFβ would be avoided, since TGFβ's are believed to increase the deposition of fibrous tissue. Suprisingly, it has now been discovered that TGFβ-3 has the opposite effect to that expected, in that it promotes healing without promoting the deposition of fibrous tissue.

The present invention provides the use of a TGFβ-3 for the manufacture of a medicament for the treatment of a fibrotic disease.

The present invention also provides a method of treating a fibrotic disease by administering a pharmaceutically effective amount of TGFβ-3 to a patient in need thereof.

The present invention also provides an agent for treating a fibrotic disease which comprises TGFβ-3 as active ingredient.

The present invention also provides a pharmaceutical composition comprising a higher proportion of TGFβ-3 in relation to TGFβ-1 or TGFβ-2, compared with relative proportions in naturally occuring TGFβ, and a pharmaceutically acceptable carrier.

EP 0 433 225 defines the biological activity of the TGFβ's ie. TGFβ-1, TGFβ-2 and TGFβ-3, as including the ability to increase formation of fibrous granular tissue in and around wound implants in rats (page 5, lines 17–19), while U.S. Pat. No. 4,810,691 and U.S. Pat. No. 4,774,228 describe the use of TGFβ's for promoting connective tissue deposition.

Experiments described in detail below indicate that contrary to the conventional view that TGFβ-3 acts in the same manner as TGFβ-1 and TGFβ-2 to increase fibrosis at the site of wound healing, it has in fact the opposite effect and promotes wound healing with reduced fibrosis and scarring.

Experiments

The experiment have involved exogenous injection of TGFβ-1, TGFβ-2 or TGFβ-3. They have also involved the injection of neutralising antibodies to TGFβ-1 or TGFβ-2 (or anti TGFβ-1 and TGFβ-2 in combination). Neutralising antibodies to TGFβ-3 are not yet available. The experimental protocol was as described in Shah et al, The Lancet, 339, 213–214, 1992).

These experiments produced a very interesting and unexpected set of results. First, the neutralising antibody to TGFβ-1 diminished scarring, i.e. reduced the amount of extracellular matrix, reduced angiogenesis and reduced the numbers of macrophages and monocytes at the wound. It also improved the orientation of collagen fibres in the healing wound. The neutralising antibody to TGFβ-2 had very little effect on its own, but showed a slight improvement in scarring. Combined, the neutralising antibodies to TGFβ-1 and TGFβ-2 showed a marked improvement in wound healing (similar to that described in Shah et al, The Lancet, 339, 213–214, 1992), namely decreased extracellular matrix deposition (decreased fibronectin, decreased collagen), decreased angiogenesis, decreased macrophages and monocytes at the wound site and better orientation of collagen and fibronectin within the wound. Exogenous addition of TGFβ-1 or TGFβ-2 had the expected result, namely of increasing extracellular matrix deposition and angiogenesis. However, exogenous addition of TGFβ-3 did not have this effect, but rather produced effects similar to those observed with the neutralising antibodies to TGFβ-1 and TGFβ-2, namely, a reduction in the amount of extracellular matrix deposited, a decrease in macrophages and monocytes and a marked improvement in subsequent scarring.

Specific details of the experiments to document the TGFβ-3 effect are as follows:

Adult male Sprague-Dawley rats (200 to 250 gram weight) were anaesthetised with halothane nitrous oxide and oxygen inhalation. Two incisions, ten millimeters in length and to the depth of the parniculous carnosis were made in the dorsal skin, equal distant from the midline and between the fore and hind limbs. The wounds were left unsutured to heal by secondary intention to produce the greatest amount of granulation tissue and scarring. In each animal, one wound (control) was unmanipulated. In different animals the other wound received a) an injection of transforming growth factor beta 1 (TGFβ-1) (20 ng per injection), or b) an injection of TGFβ-2 (20 ng per injection) or c) an injection of TGFβ-3 (20 ng per injection). It had previously been determined from dose response experiments that 20 ng per injection was the optimum dose to give. Injections were of 100 microliters in phosphate buffered saline and were introduced into the wound margins by local infiltration on days 0, 1 and 2. The fluid was infiltrated along the length of each wound margin through a single entry point 0.5 cm distal to the caudal end of the wound. At least four animals were killed by chloroform overdose on each of day 7, 14 and 42 after wounding. The wounds were processed for routine histological examination, particularly using connective tissue stains such as Mallory or Masson's trichrome. They were also processed for immuno-cytochemistry, using antibodies to detect fibronectin (as a marker of early wound repair and to show the orientation of extracellular matrix molecules), macrophages and monocytes (as an indication of the inflammatory response), laminin (to highlight basement membranes, e.g. of newly formed blood vessels) and collagen types I and III to document connective tissue deposition within the wound and scarring.

SUMMARY OF RESULTS

Compared to control wounds, at 7 and 14 days, the TGFβ-3 treated wounds had less fibronectin and the fibronectin fibres were in a better orientation. By six weeks, the fibronectin in all wounds was similar in quantity to that of the surrounding normal skin. However, that in the TGFβ-3 treated wound had a much better orientation than the other wounds. The results were almost indistinguishable from the results obtained with neutralising antibodies to TGFβ-1 and TGFβ-2. By comparison, wounds treated with TGFβ-1 orTGFβ-2 showed a vastly increased quantity of fibronectin in the wound at 7 days and this fibronectin had an abnormal orientation, compared to the surrounding tissue. The same was true at 14 days, but by 6 weeks there was little difference between the TGFβ-1 or TGFβ-2 treated wounds and the control in terms of the quantity of fibronectin present.

At 7 days TGFβ-1 treated and TGFβ-2 treated and control wounds showed similar profiles of macrophage and monocyte infiltration (for example control 159, TGFβ-1 149, control 117, TGFβ-2 112 per section). However, TGFβ-3 treated wounds had a low profile of macrophage plus monocyte infiltration (control 130, TGFβ-2 91 per section).

At 7 days TGFβ-1 treated and TGFβ-2 treated wounds had a higher profile of macrophages in the lower half of the wounds compared to similar areas in the control wounds (control 50/TGFβ-1 80, control 45/TGFβ-2 59 per section). However, in the upper half of the wounds the macrophage infiltration was similar in the TGFβ-1 treated and control wounds (control 37, TGFβ-1 39 per section) whilst TGFβ-2 treated wounds had a lower profile (control 34, TGFβ-2 19). By contrast, TGFβ-3 treated wounds showed a lower macrophage profile throughout the entire wound, compared to the control wounds (upper half control 41, TGFβ-3 16; lower half control 72, TGFβ-3 28 per section).

Laminin staining was used as a marker of neovascularisation. At 7 days, TGFβ-1 treated wounds showed an increase in the number of blood vessels, particularly at the base of the wound. TGFβ-2 treated wounds appeared similar to the control wounds. TGFβ-3 treated wounds, however, had many more blood vessels compared to either the control or the TGFβ-1 or the TGFβ-2 treated wounds. This was a very marked effect.

By 14 days there were few differences in the number of blood vessels between either the TGFβ-1, TGFβ-2 or TGFβ-3 treated wounds compared to the control. However, the TGFβ-3 treated wounds tended to have more blood vessels.

In terms of collagen deposition within the wound, as assayed by Mallory staining or immunocytochemistry, treatment of the wound with either TGFβ-1 or TGFβ-2 increased the amount of collagen within the wound on days 7 and 14 after wounding. Furthermore, this collagen had an abnormal orientation with a much higher percentage of fibres orientated in a vertical direction, compared to the surrounding dermis. At six weeks, the control, TGFβ-1 and TGFβ-2 treated wounds were visibly scarred with an abnormal accumulation of abnormally orientated collagen within the wounded area. By contrast, wounds treated with TGFβ-3 showed slightly less collagen deposition on days 7 and 14 after wounding. Moreover, the collagen deposited was in a similar reticular pattern to that of the surrounding dermis. Consequently, by six weeks after wounding, the TGFβ-3 treated wounds had a more similar dermal architecture to that of the surrounding normal skin, compared to either the control TGFβ-1 or TGFβ-2 treated wounds. This result with TGFβ-3 is very similar to that obtained with neutralising antibodies to TGFβ-1 and TGFβ-2.

In summary, therefore, treatment of the wounds with TGFβ-3 decreased the amount of extracellular matrix deposited in the early wound, assured that the orientation of this matrix was in the normal reticular pattern of the dermis, compared to the abnormal pattern of the scar, decreased the number of macrophages and monocytes and hence inflammatory infiltrate into the wound, but greatly increased the number of blood vessels in the early healing wound. These effects are almost identical to those observed with neutralising antibodies to TGFβ-1 and TGFβ-2 except the increase in the number of blood vessels. Treatment of the wounds with neutralising antibodies to TGFβ-1 and TGFβ-2 decrease the amount of extracellular matrix deposited, alter the orientation of this matrix, so that it is in a more normal alignment, decrease the inflammatory infiltrate of macrophages and monocytes (like TGFβ-3) but decrease the number of blood vessels (unlike treatment with TGFβ-3 which increases the number of blood vessels).

TGFβ-3 therefore acts as an anti-scarring (anti-fibrotic) agent. It is very clear that this is an isoform specific effect within the TGFβ family.

TGFβ-3 therefore becomes a target as an anti-fibrotic agent or an anti-scarring agent. It may be capable of biological modification to increase the anti-fibrotic effect or define more carefully that portion of the molecule responsible for these effects. It may be possible to optimise the structure of TGFβ-3 as an anti-fibrotic agent, based on such analysis. The effects of TGFβ-3 in this regard are unpredictable from the literature, and interestingly, differ from the neutralising antibody experiments, particularly in the increase in angiogenesis. This may actually be beneficial for certain kinds of wound healing, e.g. chronic wounds such as venous leg ulcers, where one wants to increase the vascular supply to stimulate healing but decrease subsequent scarring.

In the context of fibrosis, the effects of TGFβ-3 or anti TGFβ-1/TGFβ-2 agents are not limited to preventing further increases of fibrosis. TGFβ-1/TGFβ-2 act to increase the accumulation of extracellular matrix molecules both by stimulating synthesis of new extracellular matrix molecules and decreasing the removal of existing matrix molecules, i.e. inhibiting tissue turnover (Roberts and Sporn, the transforming growth factor—β's, In: Peptide growth factors and their receptors, Springer Verlag, Berlin, 1990, p 418–472). Therefore, any agent which antagonises or neutralises or renders ineffective TGFβ-1/TGFβ-2 not only decreases extracellular matrix synthesis but also increases remodelling. As an anti-fibrotic agent either TGFβ-3 or anti-TGFβ-1/anti-TGFβ-2/anti-PDGF (or some combination thereof) may in certain fibrotic diseases, e.g. glomerulonephritis, pulmonary fibrosis, reverse the accumulation of fibrous scar tissue already present in the tissue.

It will be appreciated that it is not intended to limit the invention to the above examples only, many variations, such as might readily occur to one skilled in the art, being possible, without departing from the scope thereof as defined in the appended claims.

Thus for example, as well as applying a preparation to a wound containing TGFβ-3 only, this may be given in combination with fibrotic growth factor neutralising agent (s), for example, anti-TGFβ-1 and/or anti-TGFβ-2 and/or anti-PDGF antibodies, in a ratio which will enable the required amount of vascularisation for the particular type of wound to be provided whilst at the same time healing the wound without scarring.

What is claimed is:

1. A method of inhibiting fibrosis in a patient in need thereof comprising providing said patient with an amount of transforming growth factor consisting essentially of TGF-$\beta_3$ sufficient to effect said inhibition.

2. The method according to claim 1 wherein said TGF-$\beta_3$ is provided in an inactive form that is converted to an active form.

3. The method according to claim 1 wherein said TGF-$\beta_3$ is provided in a pharmaceutically acceptable carrier.

4. A method of reducing scarring during healing of a wound in a patient in need thereof comprising providing at the site of said wound an amount of transforming growth factor consisting essentially of TGF-$\beta_3$ sufficient to effect said reduction in scarring.

5. The method according to claim 4 wherein said TGF-$\beta_3$ is provided at said site in an inactive form that is converted to an active form at said site.

6. The method according to claim 4 wherein said TGF-$\beta_3$ is provided at said site in a pharmaceutical composition comprising a pharmaceutically acceptable carrier.

7. A method of inhibiting fibrosis in a patient in need thereof comprising providing said patient with an anti-fibrotic agent selected from the group consisting of and anti-TGF-$\beta_1$, and anti-TGF-$\beta_2$ and an anti-PDGF antibody and an amount of transforming growth factor consisting essentially of TGF-$\beta_3$ sufficient to effect said inhibition.

8. The method according to claim 7 wherein said TGF-$\beta_3$ is provided at said site in an inactive form that is converted to an active form at said site.

9. The method according to claim 7 wherein said TGF-$\beta_3$ is provided at said site in a pharmaceutical composition comprising a pharmaceutically acceptable carrier.

10. A method of reducing scarring during healing of a wound in a patient in need thereof comprising providing said patient with an anti-fibrotic agent selected from the group consisting of an anti-TGF-$\beta_1$, an anti-TGF$\beta_2$ and an anti-PDGF antibody and an amount of transforming growth factor consisting essentially of TGF-$\beta_3$ sufficient to effect said inhibition.

11. The method according to claim 10 wherein said TGF-$\beta_3$ is provided at said site in an inactive form that is converted to an active form at said site.

12. The method according to claim 10 wherein said TGF-$\beta_3$ is provided at said site in a pharmaceutical composition comprising a pharmaceutically acceptable carrier.

* * * * *

UNITED STATES PATENT AND TRADEMARK OFFICE
CERTIFICATE OF CORRECTION

PATENT NO.   : 6,331,298 B1  Page 1 of 1
DATED        : December 18, 2001
INVENTOR(S)  : Ferguson et al.

It is certified that error appears in the above-identified patent and that said Letters Patent is hereby corrected as shown below:

<u>Column 6,</u>
Line 61, change "and" to -- an --; and
Line 62, change "and" (first occurrence) to -- an --.

Signed and Sealed this

Thirty-first Day of December, 2002

JAMES E. ROGAN
*Director of the United States Patent and Trademark Office*